United States Patent
Musch et al.

(10) Patent No.: US 7,144,936 B2
(45) Date of Patent: Dec. 5, 2006

(54) SOLVENT-CONTAINING COMPOSITIONS BASED ON POLYCHLOROPRENE

(75) Inventors: Rüdiger Musch, Bergisch Gladbach (DE); Knut Panskus, Leverkusen (DE); Stefan Grabowski, Dormagen (DE); Arno Nennemann, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 198 days.

(21) Appl. No.: 10/856,915

(22) Filed: May 28, 2004

(65) Prior Publication Data

US 2004/0254283 A1 Dec. 16, 2004

(30) Foreign Application Priority Data

May 30, 2003 (DE) ............... 103 24 305

(51) Int. Cl.
*C08K 3/34* (2006.01)
(52) U.S. Cl. ............... 524/273; 524/493; 524/588; 524/783
(58) Field of Classification Search ........... 524/273, 524/493, 588, 783
See application file for complete search history.

(56) References Cited

U.S. PATENT DOCUMENTS

| | | |
|---|---|---|
| 1,253,668 A | 1/1918 | Chappell |
| 2,234,215 A | 3/1941 | Youker ............... 260/89 |
| 3,397,173 A | 8/1968 | Collette et al. ........ 260/45.9 |
| 3,422,045 A | 1/1969 | Aho ............... 260/27 |
| 3,887,539 A | 6/1975 | Barth ............... 260/19 UA |
| 3,920,623 A | 11/1975 | Khan ............... 260/92.3 |
| 3,929,752 A | 12/1975 | Cooper et al. ........ 260/92.3 |
| 3,932,355 A | 1/1976 | Barney et al. ........ 260/63 HA |
| 4,124,754 A | 11/1978 | Miller ............... 526/220 |
| 4,141,875 A | 2/1979 | Brizzolara et al. ....... 260/29.7 |
| 4,704,441 A | 11/1987 | Musch ............... 526/220 |
| 6,710,091 B1 | 3/2004 | Womelsdorf et al. ........ 516/33 |
| 2002/0149002 A1 | 10/2002 | Womelsdorf et al. .... 252/363.5 |

FOREIGN PATENT DOCUMENTS

| | | |
|---|---|---|
| CA | 2162914 | 9/1995 |
| DE | 101 63 256 | 7/2003 |
| JP | 60-31510 | 2/1985 |
| JP | 11-209523 | * 8/1999 |

OTHER PUBLICATIONS

Adhäsion Jg. 10, (month unavailable) 1966, pp. 296-299, R.R. Garrett and R.D. Lawrence, "Beeinflussung der Phasenbildung in Neoprene-Lösungsmittelklebern durch bestimmte Faktoren".
Klebharzen (Adhesive resins), R. Jordan and R. Hinterwaldner editors, (Hinterwaldner Publishers, Munich) (month unavailable) 1994, Alois Kwasniok, Stephan Schröter, pp. 117-138 (see p. 124) - "Phenolharze".
Ullmanns Encyclopädie der technischen Chemie (Ullmann's Encyclopedia of Industrial Chemistry) vol. 9, (month unavailable) 1957, pp. 366-367, "Kautschuk".
Encyclopedia of Polymer Science and Technology, vol. 3, (month unavailable) 1964, pp. 705-730, "2-Chlorobutadiene Polymers".
Methoden der Organischen Chemie, (Methods of Organic Chemistry) (Houben-Weyl) XIV/1, (month unavailable) 1961, pp. 738-748, H. Logeman, "Polymerisation der wichtigsten Monomeren".
Handbook of Adhesives, Chapter 21, (month unavailable) 1977, pp. 343-367, Murray Steinfink, "Neoprene Adhesives: Solvent and Latex".
Progress in Colloid and Polymer Science, 107, (month unavailable) 1997, pp. 180-188, H.G. Müller, "New contributions of analytical ultracentrifugation to the investigation of dispersions".

* cited by examiner

*Primary Examiner*—Bernard Lipman
(74) *Attorney, Agent, or Firm*—Michael A. Miller

(57) ABSTRACT

Solvent-containing compositions based on polychloroprene, and solvent-containing zinc oxide dispersions which are stable in storage, that can be used in adhesive and sealant compositions. The compositions can be prepared by mixing the polychloroprene composition and zinc oxide dispersion and optionally adding conventional adhesive auxiliaries and/or additives and optionally adding an additional solvent.

26 Claims, No Drawings

SOLVENT-CONTAINING COMPOSITIONS BASED ON POLYCHLOROPRENE

CROSS REFERENCE TO RELATED PATENT APPLICATION

The present patent application claims the right of priority under 35 U.S.C. §119 (a)–(d) of German Patent Application No. 103 24 305.4, filed May 30, 2003.

BACKGROUND OF THE INVENTION

1. Field of the Invention

The present invention relates to solvent-containing compositions based on polychloroprene, to solvent-containing zinc oxide dispersions which are stable during storage, to processes for their production, to their use in solvent-containing polychloroprene formulations and to their use as additives in contact adhesives for inorganic or organic substrates.

2. Description of the Prior Art

Polychloroprene is a highly important raw material today as a component for making rubber adhesives, since contact adhesives can be produced therefrom.

These contact adhesives can be applied using simple devices, such as for example brushes, knives or rollers and they adhere excellently to many materials on whose rough surfaces they become firmly anchored. An even greater reason for the widespread use of contact adhesives is, however, their ability to form adhesive layers which, after a brief drying period, become apparently dry to the touch and produce bonds of immediately detectable strength on being joined with slight pressure during their "contact adhesion period," "tack time" or "open time". The immediate onset of crystallization of the polychloroprene allows the bonds to "set" quickly by a rapid increase in strength until the end point is reached.

A major disadvantage of these solvent-containing contact adhesives is the unsatisfactory storage stability of the formulations, which is manifested by phase separation caused by the following factors:
1. Dispersed stabilizers, such as magnesium dioxide and zinc oxide, which are present in dispersed form in the adhesive formulation tend to settle out of the dispersion and form sediments during the storage of the adhesive.
2. In addition, phase separation or so-called "phasing" can occur, i.e. a resin/metal oxide mixture can be flocculated from the formulation during storage.

The addition of magnesium oxide and zinc oxide to adhesives based on polychloroprene is known from the prior art. The presence of these metal oxides has an advantageous effect on the storage stability of the adhesives and on the stability of the adhesive bonds. This effect is based on the fact that polychloroprene has a tendency to cleave off small quantities of hydrogen chloride during storage, for which the metal oxides serve as acceptors.

The addition of about 4% each of magnesium oxide and zinc oxide, based on the rubber content, has proven to be advantageous.

Instead of the oxides, the carbonates of these metals are occasionally also used; zinc carbonate has a more transparent appearance in the adhesive than zinc oxide.

In the past, polychloroprene was for example masticated prior to the production of the adhesive, the oxides being incorporated using a roller or an internal mixer. If non-masticated polychloroprene was used in addition to masticated polychloroprene, the oxides were added to the masticated component. It was also possible to produce polychloroprene/metal oxide mixtures having a high metal oxide content (the masterbatch) and to then add this masterbatch to the adhesive mixtures in the required quantities. For reasons of cost this method is however hardly ever used today.

Currently only non-masticated polychloroprene is used, the oxides and carbonates usually being pasted beforehand in machines commonly used in the coatings industry.

The production of storable polychloroprene adhesives which are resistant to sedimentation and phasing is not possible using the abovementioned methods, particularly in the case of low-viscosity adhesive formulations. It is basically possible to improve their resistance to sedimentation by increasing their viscosity. This does however have the disadvantage that the compositions are more difficult to apply.

The resistance to the cleavage of HCl in the prior art polychloroprene adhesives also leaves room for improvement.

The addition of resins to polychloroprene adhesives is also known. The use of heat-reactive phenol or alkylphenol resins for the production of polychloroprene adhesives allows an improvement in the heat resistance of the adhesive bonds, since these resins form a high-melting complex compound with magnesium oxide which is readily soluble in organic solvents.

The complex formation between the metal oxide and the alkylphenol resin takes place particularly rapidly with MgO in toluene as the solvent, the reaction being considerably accelerated by the use of a small quantity of water (about 1%, based on the resin). Using this method, soluble complexes are formed in organic solvents and modified MgO is formed on the surface, so that MgO can no longer form a sediment. A description of this complex formation can be found in: R. Garrett, R. D. Lawrence, Adhesion Jg. 10, 1966, page 296.

This MgO/resin reaction can however only be applied to a small extent to ZnO. ZnO is known to be essentially inactive in the complex-forming reaction with the alkylphenol resin, cf: R. Jordan and R. Hinterwaldner, "Klebharze" (Adhesive resins), page 124 (Hinterwaldner Publishers, Munich, 1994).

The present invention was therefore based on the problem of providing polychloroprene adhesive compositions having improved stability, and in particular improved resistance to sedimentation, improved resistance to phasing and improved resistance to the cleavage of HCl. The invention is also based on the problem of making the ZnO used as a so-called anti-ageing agent also capable of forming complexes with phenol or alkylphenol resins so that highly heat-resistant adhesive formulations can be obtained using ZnO.

SUMMARY OF THE INVENTION

The present invention is directed to a first composition that includes:
a) polychloroprene
b) one or more organic solvents and
c) zinc oxide particles having an average particle size of less than 150 nm.

The present invention is also directed to a second composition containing:
b) one or more non-polar organic solvents and
c) zinc oxide particles having an average particle size of less than 150 nm.

The present invention is additionally directed to a process for producing the second composition including the steps of:
  producing zinc oxide particles having an average particle size of less than 150 nm in the presence of at least one polar organic solvent,
  compacting the zinc oxide particle dispersion obtained in the above step to a solids content of at least 80% by weight, and
  redispersing the zinc oxide dispersion obtained in the above step with one or more non-polar organic solvents, optionally with the addition of one or more dispersants.

The present invention is further directed to solvent-containing adhesive compositions that include either of the first and second compositions described above.

The present invention is still further directed to a process for producing the first composition according to the steps:
  i) preparing a composition comprising b) one or more non-polar organic solvents, and c) zinc oxide particles having an average particle size of less than 150 nm,
  ii) preparing a composition containing polychloroprene dissolved in one or more organic solvents,
  iii) mixing the compositions prepared in steps i) and ii),
  iv) optionally adding conventional adhesive auxiliaries and/or additives and
  v) optionally adding an additional solvent.

The present invention is also directed to a process for producing bonded substrates that includes applying at least one of the above-described compositions to at least one surface of at least one substrate and subsequently bonding the coated substrate to at least one additional optionally coated substrate as well as to the bonded substrates so obtained.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

The inventors of the present patent application surprisingly succeeded in solving the abovementioned problems by using a particularly finely divided zinc oxide dispersion in a non-polar solvent. By using the nano zinc oxide dispersions according to the invention it is possible to obtain adhesive formulations which are stable in storage. In the presence of reactive phenol or alkylphenol resins complexes are formed.

It has been found that by combining solvent-containing polychloroprene adhesive formulations and the nano ZnO dispersions according to the invention adhesives can be produced which do not undergo sedimentation and which, in combination with reactive phenol or alkylphenol resins, form adhesives which have high heat resistance after bonding.

The present invention therefore relates to a composition which contains:
a) polychloroprene,
b) one or more organic solvents and
c) zinc oxide particles whose average particle size is less then 150 nm.

According to the invention, polychloroprene (PCP) is understood to include not only (poly(2-chloro-1,3-butadiene)) but also copolymers containing chloroprene which are produced using ethylenically unsaturated comonomers. The production of polychloroprene has been known for a long time and it is generally carried out by emulsion polymerization in an alkaline aqueous medium, cf. "Ullmanns Encyclopädie der technischen Chemie" (Ullmann's Encyclopedia of Industrial Chemistry), Vol. 9, page 366, "Urban und Schwarzenberg" Publishers, Munich/Berlin, 1957; "Encyclopedia of Polymer Science and Technology", Vol. 3, pp. 705–730, John Wiley, New York, 1964; "Methoden der Organischen Chemie" (Methods of Organic Chemistry) (Houben-Weyl) XIV/1, 738 et seq. Georg Thieme Publishers, Stuttgart, 1961.

Suitable emulsifiers for the production of PCP are basically all compounds and mixtures thereof which sufficiently stabilize the emulsion, such as for example water-soluble salts, and in particular the sodium, potassium and ammonium salts of long-chain fatty acids, rosin and rosin derivatives, relatively high molecular weight alcohol sulphates, arylsulphonic acids, formaldehyde condensates of arylsulphonic acids, non-ionic emulsifiers based on polyethylene oxide and polypropylene oxide and emulsifying polymers such as polyvinyl alcohol (cf. DE-A 2 307 811, DE-A 2 426 012, DE-A 2 514 666, DE-A 2 527 320, DE-A2 755 074, DE-A 3 246 748, DE-A 1 271 405, DE-A 1 301 502, U.S. Pat. No. 2,234,215 and JP-A 60-31 510).

Polychloroprene is either used for the production of commercial rubber articles after appropriate compounding and vulcanization, or it is used as a raw material for contact adhesives. (Handbook of Adhesives; Chapter 21, Van Nostrand Reinhold, New York, $2^{nd}$ Edition, 1977).

For the production of adhesives stongly crystallizing types of polychloroprene are predominantly used which can be obtained by emulsion polymerization at low temperatures (of lower than 15° C.). The adhesives produced therefrom produce adhesive bonds which have high initial strength and which set rapidly. These properties are particularly important in all cases where the adhesive bond is exposed to high material stresses, such as for example when bonding highly arched soles in the shoe industry or curved surfaces in the furniture industry, and especially when the bonded articles have to undergo rapid further processing, such as for example on a conveyor belt.

Preferred types of polychloroprene to be used according to the invention have a solution viscosity (10% by weight in toluene) of 50–7,000 mPas at 23° C.

The composition according to the invention also contains one or more organic solvents. Organic solvents are carbon-containing solvents. The polychloroprene types of adhesives are soluble in many organic solvents and solvent mixtures. In the compositions according to the invention the polychloroprene is therefore present in dissolved form. The solvent or solvent mixture to be used for the production of the adhesive is selected on the basis of commercial and technical factors, it being necessary to take into account, inter alia, that the solvent has a considerable effect on
  the viscosity of the adhesives,
  the compatibility of the adhesives and the crosslinking agent added,
  the properties of the adhesives on being stored at low temperatures,
  the occurrence of phase separation on storing resin-containing adhesives,
  the wetting of the surfaces to be bonded,
  the drying of the adhesive films,
  the contact adhesion time of the adhesive films and
  the setting rate of the adhesive bonds.

Apart from the above effects on the technical properties of the adhesives, the physiological effect of the solvents and their flammability must also be taken into consideration.

Suitable solvents include polar and non-polar solvents. According to the invention, polar solvents are those whose solubility in water at 20° C. is higher than 0.1% by weight, based on the quantity of the water. Such solvents include, for example, halogenated aliphatic hydrocarbons, aliphatic esters, such as ethyl acetate, etc. and aliphatic ketones, such as acetone, methyl ethyl ketone, etc. and alcohols, such as n-butanol. The polar solvents are preferably those which are miscible with aliphatic or aromatic hydrocarbons at room temperature without phase separation and preferably in any desired mixing ratio.

Since the ZnO dispersions according to the invention are preferably used for the production of the compositions according to the invention, the polychloroprene adhesive compositions according to the invention preferably contain at least one non-polar solvent of the kind used for the production of the ZnO dispersions, as described below. According to the invention, "non-polar solvents" are understood to be those which are essentially immiscible with water, i.e. whose solubility in water at 20° C. is less than 0.1% by weight, based on the quantity of the water. Conversely, for example, less than 0.1% by weight of water dissolves in such solvents at 20° C. Preferred solvents/media are also those whose dielectric constant (DC) is <5, and in particular those whose DC is <3. The following can for example be used: aliphatic hydrocarbons and/or aromatic hydrocarbons having a variable chain length, degree of branching and molecular weight, paraffinic, naphthenic and aromatic oils and waxes and long-chain esters, alcohols, ketones, ethers, halogenated aliphatic and/or aromatic hydrocarbons and combinations/mixtures thereof. Aliphatic, branched, straight-chain, cyclic or aromatic hydrocarbons, such as pentane, hexane, cyclohexane, heptane, octane, benzene, toluene, xylene, etc. and mixtures such as solvent naphtha, are preferred.

According to the invention, mixtures of the abovementioned polar and non-polar solvents are particularly preferred. A preferred solvent mixture consists of aliphatic esters or alcohols and aliphatic and aromatic hydrocarbons.

The compositions according to the invention are solvent-based compositions. They therefore essentially contain no water. They may however contain a quantity of at most about 1% by weight, and preferably at most about 0.5% by weight of water.

The compositions according to the invention also contain zinc oxide particles whose average particle size is less than 150 nm, preferably less than 100 nm and more preferably less than 50 nm. Since the zinc oxide particles are not spherical, reference is made to average particle size as opposed to average particle diameter.

The zinc oxide particles can be present in the compositions according to the invention both in the form of so-called primary particles and in the form of agglomerates. According to the invention, the term "average particle size of the ZnO particles" refers to the average particle size determined by ultracentrifugation and includes the size of primary particles and any agglomerates thereof which may be present (cf: H. G. Müller, Prog. Colloid Polym. Sci. 107, 180–188 (1997)). The values refer to weight average.

The weight-averaged average particle size of the ZnO particles determined by ultracentrifugation is at most 150 nm and preferably at most 100 nm and particularly preferably at most 50 nm, at least 90% by weight of all of the particles preferably being smaller than 200 nm, preferably smaller than 150 nm and particularly preferably smaller than 100 nm.

An average particle size of greater than 150 nm is disadvantageous since there is then the danger of sedimentation and the ZnO is less active and virtually non-reactive with the phenol resins.

By means of TEM photographs (transmission electron-microscopic photographs) it is also possible to determine the number-average particle size of the ZnO primary particles by counting and statistical analysis according to WO 00/50503. As already mentioned above the term "primary particles" refers according to DIN 53206; 1992–08 to particles identifiable as individual particles by suitable physical processes. The average particle size of the primary particles is at most 100 nm, preferably at most 50 nm, more preferably at most 30 nm, and even more preferably at most 15 nm.

The zinc oxide particles are added to the compositions according to the invention preferably in the form of ZnO dispersions in at least one non-polar organic solvent whose zinc oxide particles have an average particle size of less than 150 nm. The reason for this is as follows. In order to dissolve the polychloroprene, a non-polar organic solvent is indispensable in practice. The addition of a ZnO dispersion in a polar organic solvent, as described in the prior art, to a polychloroprene solution in a non-polar solvent, generally results in segregation or phase separation.

The use of nano zinc oxide dispersions for various applications is known from the prior art (see for example WO02/083797).

The production of aqueous dispersions of zinc oxide having an average particle size of <100 nm is described in various publications:

I) An aqueous dispersion containing zinc oxide agglomerates having an average particle diameter of <100 nm, and preferably 20–60 nm, is described for example in WO95/24359. Such dispersions can be produced for example by the process described in WO95/24359 by grinding in the presence of a dispersant such as for example polyacrylic acid.

II) A zinc oxide sol is described for example in WO 00/50503 which is produced by redispersing zinc oxide gels having a primary particle diameter of <=15 nm. Suitable solvents are water or water/ethylene glycol mixtures, to which surface-modifying compounds are optionally added.

III) Zinc oxide sols having average primary particle diameters of <30 nm and average agglomerate diameters of <200 nm are described for example in WO 02/083797.

IV) Zinc oxide dispersions obtainable by surface modification with an oligo- or polyethylene glycol acid are described for example in DE-A 10 163 256.

In addition, the production of zinc oxide dispersions in polar organic solvents having an average particle size of <100 nm is described in the literature.

I) WO 00/50503 describes, inter alia, the production of zinc oxide sols in preferably dipolar/aprotic solvents, such as for example dichloromethane and/or chloroform, by the redispersion of nanoparticulate zinc oxide gels.

II) DE 10 163 256 describes the dispersion of zinc oxides obtainable by surface modification with an oligo- or polyethylene glycol acid, in polar solvents such as alcohols or acetone.

The production of the zinc oxide dispersions used according to the invention in non-polar organic solvents has not previously been described.

The abovementioned processes are not suitable for producing longterm-stable nanoparticulate zinc oxide dispersions in non-polar organic solvents or other non-polar media (such as for example hydrocarbon resins). Due to the polar nature of the zinc oxide particle surface it is necessary to produce the particles in a polar medium and to stabilize the particles in this medium in order to avoid irreversible agglomeration and to obtain dispersibility.

The problem on which the present invention was based was therefore that of transferring the zinc oxide particles produced in a polar medium (solvent and/or water) to a non-polar medium (solvent or other non-polar matrix) and dispersing them in said medium without the occurrence of irreversible agglomeration or instability of the dispersion.

The problem is in particular the fact that the non-polar media according to the invention and the abovementioned polar media do not mix and they form two phases. Phase transition is therefore necessary for transferring the particles from the polar phase to the non-polar phase. This is for example possible by liquid/liquid phase transfer or solid/liquid phase transfer.

It is therefore surprising that the zinc oxide particles in the process according to the invention do not irreversibly agglomerate on leaving the stabilizing polar phase but are redispersed on entering the non-polar phase.

As already explained above, non-polar solvents or non-polar media according to the invention are those which are not miscible with water, i.e. whose solubility in water is <0.1% at 20° C. and in which <0.1% water dissolves at 20° C. Such solvents/media are preferred whose dielectric constant is <5, and in particular those whose DC is <3. The following can for example be used: aliphatic hydrocarbons and/or aromatic hydrocarbons having a variable chain length, degree of branching and molecular weight, paraffinic, naphthenic and aromatic oils and waxes and long-chain esters, alcohols, ketones, halogenated aliphatic and/or aromatic hydrocarbons and combinations/mixtures thereof.

According to the invention, the zinc oxide dispersions in non-polar solvents/media are produced by redispersing zinc oxide gels produced for example as described in WO 00/50503, optionally using dispersants and/or stabilizers, to form storable non-sedimenting ZnO dispersions in non-polar organic solvents.

In WO 00/50503 it is stated that a particularly high degree of compaction is a necessary requirement for the effective dispersibility of the zinc oxide gels. This is explained by the components of the surrounding matrix being separated off as completely as possible. Only such gels are however described whose content by weight of zinc oxide is <80%. The density of zinc oxide is 5.6 g/cm$^3$ and the density of methanol is 0.8 g/cm$^3$. This corresponds to a volumetric degree of filling of <36%. It can therefore be assumed that the particles are essentially individually separate from each other in the matrix or are at least surrounded by a matrix shell.

In contrast to the zinc oxide gels described in WO 00/50503 the gels used in the examples of the invention have a solids content of >80%, and preferably >90% to >95%, based on the weight of the gels. This high solids content is necessary for the phase transfer to non-polar solvents, since the polar (methanolic) matrix is not miscible with the non-polar matrix. For the gels described in the present context this corresponds to a volumetric degree of filling of >36%, and preferably >56% to >73%. At such high degrees of filling it would be assumed that the particles are no longer completely separated from each other by the matrix and that at least to a certain extent direct particle-to-particle contacts are formed. This would mean that such gels can no longer be redispersed without considerable effort. It was therefore surprising that according to the invention these gels can be completely redispersed unproblematically in non-polar organic solvents.

In addition to the use of zinc oxide gels in aqueous dispersions the present invention also relates to the further compaction of nanoparticulate zinc oxide gels having a solids content of <80% and producible for example according to WO 00/50503, in such a manner that a solids content of >80%, and preferably >90 to >95% is obtained, whereby the simple, spontaneous redispersibility in non-polar media is made possible and simultaneously the simple, spontaneous redispersibility in polar solvents and water at a lower degree of compaction, as described in WO 00/50503, is retained.

The nanoparticulate zinc oxide dispersions according to the invention are produced according to the invention by further compacting corresponding gels in polar organic solvents having a solids content of <80%, as produced for example according to WO 00/50503, by centrifugation, flocculation, extraction or distillation or any other desired process for removing the matrix surrounding the particles, while avoiding the formation of irreversible particle-to-particle contacts. This is appropriately effected by the following steps:

1. Destabilizing, reactive accompanying substances, and in particular salts dissolved in the matrix are already appropriately substantially separated off prior to compaction (the separation can take place by separating off the phases containing the abovementioned undesired components).
2. The reactivity of the particles is reduced by limiting the temperature during the production and working-up of the ZnO particles appropriately to <100° C., preferably to <80° C. and particularly preferably to <60° C.

Dispersants can be added to the ZnO dispersion obtained according to the invention. Suitable dispersants are long-chain ($C_5$–$C_{20}$) carboxylic acids and sulphonic acids which are at least partially soluble in the non-polar medium, for example in quantities of 0.01 to 1 mmol per g of ZnO. Preferred dispersants are long-chain ($C_5$–$C_{20}$) carboxylic acids, such as for example oleic acid. In addition, stabilizers such as for example monohydric or polyhydric alcohols or polyethers can be added to the ZnO dispersions used according to the invention.

A particularly preferred variant of the ZnO dispersion according to the invention is one resulting from the reaction with at least one phenolic resin. Phenolic resins are synthetic resins which are obtained by the condensation of phenols with aldehydes, and in particular formaldehyde, by derivatization of the resulting condensates or by the addition of phenols to unsaturated compounds, such as natural resins. According to the invention the condensation products of phenols and aldehydes are preferably used. Preferably alkylphenols (cresols, xylenols, nonyl- and octylphenol) and aryl derivatives and dihydric phenols are used in addition to phenol as the phenol component. Alkylphenol resins are particularly preferred. In a preferred variant they are added to the ZnO dispersions according to the invention and allowed to react at room temperature or elevated temperatures. In the case of the ZnO dispersions according to the invention, soluble ZnO complexes are surprisingly formed, just as in the case of MgO, and surface modification surprisingly takes place which counteracts the sedimentation of the ZnO nanoparticles.

The polychloroprene composition according to the invention can also contain d) auxiliaries and/or additives commonly used for adhesives. Such auxiliaries and/or additives can include, but are not limited to solvents, plasticizers, pigments, fillers, resins, catalysts, levelling agents, thickeners, stabilizers, light stabilizers, antioxidants, defoamers, UV absorbers and combinations thereof. Specific auxiliaries and/or additives include for example the following:

Fillers

Fillers of the most diverse kinds can be added in any desired quantities to the polychloroprene adhesives. Highly filled mixtures are luting clays mainly of the gap-filling kind. Suitable fillers are for example kaolin, chalk, barite, quartz powder, asbestos powder, carbon black and silica.

Additives of about 50 to 100%, based on the polymer content, are commonly used. Kaolin or chalk are for example added to such adhesives. They are used for bonding floor coverings.

Carbon black and silica fillers increase the cohesive strength of the adhesive film, although carbon black can only be used in rare cases due to its colour. In too high quantities silica fillers impair the contact bonding, so that all-over bonding does not occur.

If the filler is however required to be distributed as finely as possible it should be incorporated using a roller—or even better—an internal mixer. Pasting in machines commonly used for coatings is also possible.

If the adhesives are to be coloured in any particular shade coloured pigments can be incorporated in the same way as the fillers.

Resins

Using solutions of the strongly crystallizing types of polychloroprene which merely contain metal oxides, compounds of high strength are obtained even without any further additives. These adhesives have rapid setting capacity. Their short contact adhesion period is however less advantageous.

By adding resins the contact adhesion period can be adjusted over a wide range and the setting time can be accelerated. The final state of the crystallization of polychloroprene is not substantially impaired by resins, so that high cohesive strength of the adhesive films is obtained. Liquid, plastic, hard and brittle resins exist. They can be used for increasing or decreasing the elasticity of the adhesive film to match the material to be bonded. The resins are soluble without producing any significant increase in viscosity. They can therefore be contained in the adhesive in relatively large quantities.

Numerous natural and synthetic resins, such as for example ethylene, glycerol and pentaerythritol esters of unmodified, hydrogenated and dimerized rosin fulfil the basic requirement of compatibility with polychloroprene solutions. The same applies to rosin esters modified by phenol resins, of the kind obtained from low molecular weight phenol/formaldehyde condensates and rosin followed by esterification, and to terpene phenol and cumarone resins. Particularly important is their compatibility with heat-reactive alkylphenol resins obtained from alkylphenols, such as for example butyl or octylphenol and formaldehyde in an alkaline medium, as already mentioned above.

In a preferred variant of the invention the composition preferably contains at least one additional polymer or resin. This resin is preferably an alkylphenol/formaldehyde resin of the kind obtainable for example on the market, such as Alresen® PA 565, SP 134 (Schenectady).

The resins are usually added in a quantity of about 10 to 50%, based on polychloroprene, although they can also be used in higher quantities.

In order to prolong the contact adhesion period terpene phenol resins, low-melting rosin esters and cumarone resins can above all be used. Rapid setting of the bonds, i.e. the quickest possible obtainment of the final strength, is obtainable with high-melting rosin esters or heat-reactive alkylphenol resins, although the contact adhesion period is reduced thereby.

Chlorinated Rubber

When using terpene phenol resins, low-melting rosin esters and/or cumarone resins as tackifiers for producing polychloroprene adhesives it is possible to considerably increase the initial strength of the bonds by adding 5–10 parts of chlorinated rubber. Chlorinated rubber is generally used.

Anti-Ageing Agents

Polychloroprene itself is considerably more resistant to ageing than many of the resins used for the production of adhesives. Since rosin esters, cumarone resins and terpene phenol resins are unsaturated compounds, they undergo oxidation over time. This is initially manifested by the embrittlement or softening of the adhesive layer in the peripheral zones of the bond and can finally result in the complete destruction of the adhesive bond. The addition of suitable antioxidants can counteract the ageing of polychloroprene adhesive bonds.

Sterically hindered phenols, such as Vulkanox® KB, Vulkanox® DS and Vulkanox® BKF, are optimally suitable for resin-containing polychloroprene adhesives. In a quantity of 2%, based on the polymer, these antioxidants provide effective protection and their tendency to discolour under the effect of light and contact is low. Vulkanox® BKF provides particularly long-lasting protection against ageing, as required for example for adhesive bonds in the furniture sector.

In addition, the ZnO added according to the invention acts as an anti-ageing agent, and in particular as an agent for absorbing HCl with the formation of $ZnCl_2$. Since $ZnCl_2$ is a catalyst for the undesired crosslinking of polychloroprene, MgO is preferably added which deactivates the $ZnCl_2$ with the formation of an oxychloride.

Crosslinking Agents Based on Polyisocyanate

In the case of highly crystallizing types of polychloroprene the cohesive strength of the adhesive bond is considerably increased by its crystallization. This crystallization is however dependent on temperature. The adhesive films decrystallize under the effects of heat and thus decrease in strength. The resistance of the adhesive bonds to the effects of heat is improved if heat-reactive phenol resins are added to the adhesive. They increase the heat resistance to about 100–110° C.

If higher heat resistance is required, it is necessary to add polyisocyanates, such as for example Desmodur, to the adhesive solution prior to its application. Due to the crosslinking which immediately begins on adding the polyisocyanate, the immediate strength of the adhesive bonds is increased and they set more rapidly. Furthermore, the addition of polyisocyanate improves adhesion to numerous substrates which are difficult to bond.

The adhesive to which polyisocyanate has been added must be applied within a few hours, before the reaction has advanced to such an extent that gel formation takes place.

A preferred composition of the invention contains:
  4.95 to 59.95% by weight, preferably 15 to 45% by weight, of a) polychloroprene,
  40 to 95% by weight, preferably 50 to 80% by weight, of b) one or more organic solvents, 0.05 to 10% by weight, preferably 1 to 5% by weight, of
c) zinc oxide particles whose average particle size is less than 150 nm, 0 to 55% by weight, preferably 0 to 30% by weight of d) one or more conventional adhesive auxiliaries and/or additives.

A particularly preferred composition of the invention contains:
a) 5–50% by weight of polychloroprene having a solution viscosity (10% in toluene) of 50–7,000 mPas at 23° C. and
c) 0.1–10% by weight of ZnO (based on the quantity of polychloroprene) in the form of a ZnO dispersion in a non-polar organic solvent having an average particle size of <150 nm, it being possible for surface-modifying compounds to be additionally contained in this dispersion and for the particles to consist either of non-agglomerated ZnO primary particles or ZnO agglomerates or mixtures of dispersed ZnO primary particles and ZnO agglomerates and
d) additional adhesive auxiliaries and additives.

The invention also relates to a process for producing the composition according to the invention which comprises the following steps:
i) preparing the ZnO dispersion according to the invention using at least one non-polar organic solvent,
ii) preparing a composition containing polychloroprene dissolved in one or more organic solvents,
iii) mixing the compositions prepared in steps i) and ii),
iv) optionally adding conventional adhesive auxiliaries and/or additives,
v) optionally adding additional organic solvents.

Step i) can also include the reaction of the ZnO dispersion after its production with the phenol or alkylphenol resin.

Machines of the most diverse types are used for the production of the compositions according to the invention. In principle the machines employed are stirring or kneading devices in which the components of the adhesives are comminuted and dissolved.

In a preferred variant of the invention, when producing the compositions according to the invention, only a portion—approximately 80% or 90%—of the total specified quantity of solvent is initially introduced into the dissolving machine so that the required viscosity can be adjusted after the production process by adding the remaining solvent.

Polychloroprene and the metal oxides, and in particular the ZnO dispersion, fillers, resins and anti-ageing agents, are added in succession with stirring to the initially introduced solvent.

The invention also relates to the use of the composition according to the invention as an adhesive or sealant.

The invention also relates to a process for producing bonded substrates which comprises applying at least one composition according to the invention to at least one surface of at least one substrate and then bonding the coated substrate to at least one additional, optionally coated substrate, as well as to bonded substrates obtained by this process.

The application of the adhesive formulations can be carried out in the known manner, for example by brushing, pouring, knife-coating, spraying, rolling or dip-coating. The drying of the adhesive film can be carried out at room temperature or at an elevated temperature.

The formulations according to the invention can be used as adhesives, for example for bonding any desired substrates of identical or different types, such as wood, paper, plastics, textiles, leather, rubber or inorganic materials, such as ceramics, stoneware, glass fibres or cement.

Contact adhesives based on polychloroprene are predominantly solvent-containing adhesives which are applied to both parts to be bonded and allowed to dry. By then joining both parts under pressure a bond having high strength at room temperature and, after adding corresponding high-melting resins, also at elevated temperatures (heat resistance), is obtained.

It is understandable that adhesives allowing such an uncomplicated and rapidly performed adhesion process are of extreme commercial importance. Polychloroprene adhesives are therefore used in all fields, e.g. in the shoe or furniture industry, where articles are to be produced in small numbers or where articles are produced in large numbers in various shapes or sizes according to individual requirements. Similarly, one main field of use is for example the building industry or shipyards, where bonding processes have to be carried out on site without the use of complicated machines, i.e. in the form of assembly work such as interior fittings or the laying of floor coverings.

EXAMPLES

1. Starting Substances:

| No | Product | Description | Supplier |
|---|---|---|---|
| 1 | Baypren ® 320 | Polychloroprene rubber; strongly crystallizing; SV (1) | Bayer MaterialScience AG |
| 2 | Baypren ® 233 | Polychloroprene rubber; moderately crystallizing; SV(1) | Bayer MaterialScience AG |
| 3 | Maglite ® DE | Magnesium oxide | C.P. Hall Company |
| 4 | Bayoxide ® Z | Active zinc oxide | Bayer Chemicals AG |
| 5 | Nano zinc oxide in an organic solvent (hexane) | Example A according to the invention | |
| 6 | Nano zinc oxide in an organic solvent (toluene) | Example B according to the invention | |
| 7 | Alresen ® PA 565 | Alkylphenol resin | Schenectady |
| 8 | SP 134 | Alkylphenol resin | Schenectady |

SV (1) = Solution viscosity 10% in toluene at 23° C.: 350–810 mPas

2. Production of the Nano Zinc Oxide Dispersions

Example A According to the Invention 1820 g of methanol and 130 g of water are initially introduced into a 4-litre flat-flange vessel at room temperature and 238 g (2.925 mol) of ZnO are added with stirring (at 200 r.p.m.). Then the reaction mixture is heated to 50° C. and 355 g (5.915 mol) of glacial acetic acid are added via a dropping funnel over a period of 15 minutes (the addition is begun at 45° C.), whereupon the temperature increases to 55° C. 1 hour after the addition of the glacial acetic acid the solution is transparent and the internal temperature is 50° C. Then 435 g of an aqueous NaOH solution (with an NaOH content of 47.82%) are weighed and added over a period of 30 mins (200 r.p.m.), during which the temperature rises from 50° C. to 57° C. After the addition is complete the temperature is adjusted to 60° C. and the mixture is stirred for 1 hour. Then the suspension is cooled to room temperature and the stirrer is switched off. After a settling period of 8 hours the transparent supernatant (2172 g) is siphoned off and the remaining suspension is stirred with 1950 g of fresh methanol for 10 minutes. After an additional settling period of 8 hours the supernatant (1845 g) is once again siphoned off and the remaining suspension is once again stirred with 1950 g of methanol for 10 minutes and again left to settle. After once again siphoning off the supernatant (1851 g) the suspension remaining as the sediment is discharged via the bottom valve and filled into a container. Weight: 800 g.

1.5 kg of n-hexane are added with stirring to 770 g of the resulting suspension. A tacky gel is obtained which rapidly settles after switching off the stirrer. The transparent supernatant is separated off. This process is repeated another two times until the supernatant is free from methanol. 260 g of a ZnO gel with a solids content of 81% are obtained. Then 35.8 g of oleic acid (0.6 mmol per 1 g of ZnO) in 616 g of n-hexane are added to the gel and the mixture is stirred for 10 minutes. The mixture is then introduced into a separating funnel. About 5 g of an aqueous phase (sodium acetate solution) are separated off and the organic phase is filtered through a filter having a pore size of 1 μm. Yield: 778 g The analytical determination reveals a zinc oxide content of 27.13%. The average particle size determined by ultracentrifugation is about 65 nm.

Example B According to the Invention

A suspension obtained according to Example A (240 g of ZnO in 560 g of MeOH) is compacted to form a gel having a zinc oxide solids content of 90% by removing the methanol in vacuo at room temperature. Then 34 g of oleic acid dissolved in 526 g of toluene (=0.5 mmol of oleic acid per g of ZnO) are added to this gel and the remaining MeOH is stripped off in a rotary evaporator. A stable, milky dispersion is obtained which is pressure filtered through a 1 μm filter.

Yield: 546 g

ZnO content: 34.05%

After storage for four weeks at room temperature no sediment is detectable.

3. Production of the Polychloroprene Adhesive Solutions 3.1 One-Pot process

The following quantities are weighed into a 300 ml bottle for the production of the polymer solution:

23.00 parts by weight of Baypren®
2.00 parts by weight of Maglite® DE
1.0 part by weight of a zinc oxide dispersion (quantity based on zinc)
10.00 parts by weight of Alresen® PA 565

Depending on the solution viscosity of the polychloroprene the solvent mixture ethyl acetate/solvent naphtha/toluene=2:2:1 (ENT) is calculated via the computational formula and added:

$Y_2 = 32 * \text{Ln}(X_2) - 61$    $X_2$ = SV of a 10% toluene polymer solution
$Y_2$ = parts by weight of solvent (ENT)

The wide-necked flask is sealed with a plastic lid containing a polyethylene seal. Then the glass flask is shaken vigorously by hand before the dissolving process in order to prevent the polymer from adhering to the glass wall or the base of the glass flask.

The dissolving process is carried out in a shaking machine R020 from the Gehardt company at a maximum shaking rate. The dissolving process is complete when the polymer has completely dissolved (inspection test). The minimum shaking period is 16 hours.

The samples to be examined are heated to 23.0° C.+/−0.1° C. in a thermostatted water bath. Care must be taken to ensure that the sample in the sealed sample vessel is immersed to such a depth in the water bath that the surface of the sample liquid is below the level of the water bath. The sample is removed from the water bath for examination after at least 60 minutes.

The adhesive mixture is then adjusted to a viscosity of 1000 mPa*s+/−100 mPa*s. The viscosity is determined in the bottle at 23° C. using a Brookfield DV II viscosimeter, spindle no. 2. ENT 221 is added for adjusting the viscosity.

If solvent is evaporated off or added according to the requirements the polymer solution must be vigorously shaken briefly by hand and then mixed for at least 15 minutes in the shaking machine at the maximum speed of rotation.

This process is repeated until the viscosity is adjusted in the viscosity range of 900–1100 mPa*s (23° C.).

After adjusting the viscosity the bottle is sealed with the PE seal and the plastic lid and stored at room temperature.

3.2 Production of the Adhesive Solution after a Preliminary Reaction with the Resin and ZnO in the Toluene Phase:

First adhesive solution: The following components are mixed and shaken for 4 hours at room temperature.

34.36 parts by weight of Schenectady ® SP 134
3.44 parts by weight of ZnO (in the form of a zinc oxide dispersion) (quantity based on ZnO)
0.34 parts by weight of distilled water
61.86 parts by weight of toluene Second adhesive solution: 23 parts of Baypren are dissolved in the remaining solvent mixture, as described in 3.1. MgO is not added. Then the solutions 1 and 2 are mixed.

3.3 Production of the Adhesive Solution for Examining Thermostability (HCl Resistance)

10 g of Baypren® 233 and 0.2 g of a zinc oxide dispersion (quantity based on the solid ZnO) are dissolved in 90 ml of toluene. A sample is immediately removed and dried over night at room temperature. Then the HCl resistance of the dry sample is determined. After a storage period of 14 days at room temperature a new sample is taken, dried and the HCl resistance determined.

4. Test Methods

4.1 Testing the Sedimentation and Phasing Properties

The same procedure is used for the production of the adhesive formulation as that described in section 3, but without the addition of magnesium oxide.

Evaluation:

The adhesive mixture is examined daily for flocculation and phase separation and assessed according to the following ratings:

0=unchanged
1=marked sediment formation
2=initial phase separation
3=slight flocculation
4=marked flocculation
5=phase separation

4.2 Determination of Thermostability (HCl Resistance)

The examination of the dried adhesive samples is carried out as described in DIN 53381, Method B.

Performance of the Examination:

Test device: 763 PVC—thermomat from Metrohm, 9101 Herisau, Switzerland

The dried adhesive samples (having a thickness of 0.1–1 mm) are cut to an edge length of about 2–3 mm, 0.5 g is weighed into a test tube and the test is carried out at 120° C. using air as the carrier gas. The electrical resistance of water in which the HCl gas formed redissolves is measured. The HCl resistance referred to is the point in time at which the electrical resistance reaches a value of 150 μS/cm. The higher the value is, the more resistant the sample tested is to the cleavage of HCl.

Results:

Determination of Sedimentation

The production is carried out as described in section 3.1, the standard ZnO being compared to the nano ZnO according to the invention (in the form of the dispersions according to the invention). The sedimentation and phasing tests are carried out under intensified conditions in order to determine the differences in the storage stability after a short time.

| Formulation | 1 | 2* |
|---|---|---|
| Baypren ®[1] | 100 | 100 |
| ZnO[1] | 4[2] | |
| Nano ZnO[1], Example A | | 4 |
| Resin PA 565[1] | 30 | 30 |
| Ethyl acetate | 136 | 136 |
| Solvent naphtha | 136 | 136 |
| Toluene | 68 | 68 |
| Sedimentation rating according to section 4.1 | | |
| Sedimentation (in days) | | |
| 1 | 0 | 0 |
| 2 | 0.5 | 0 |
| 3 | 1 | 0 |
| 5 | 1 | 0 |
| 10 | 1 | 0 |
| 14 | 2 | 0 |
| 28 | 2 | 0 |

[1]based in all cases on solids
[2]Bayoxide Z
*= example according to the invention The substitution of ZnO in formulation 1 by nano ZnO according to the invention in formulation 2 produces a formulation which is resistant to sedimentation Determination of the phasing properties in formulations according to specification 4.1

| Formulation | 3 | 4* |
|---|---|---|
| Baypren ® 320[1] | 100 | 100 |
| MgO[1] | 5 | 5 |
| ZnO[1] | 4[2] | — |
| Nano ZnO, Example A[1] | — | 4 |
| Resin PA 565[1] | 30 | 30 |
| Ethyl acetate | 136 | 136 |
| Solvent naphtha | 136 | 136 |
| Toluene | 68 | 68 |
| Phasing (in days) | | |
| 1 | 0 | 0 |
| 2 | 2 | 0 |
| 3 | 3 | 1 |
| 5 | 3 | 2 |
| 10 | 4 | 3 |
| 14 | 5 | 4 |
| 28 | 5 | 5 |

[1]based in all cases on solids
[2]Bayoxide Z
*= example according to the invention Determination of the phasing properties in formulations according to specification 3.2

| Formulation | 5 | 6* | 7* |
|---|---|---|---|
| Baypren ® 320[1] | 100 | 100 | 100 |
| ZnO[1] | 4[2] | | |
| Nano ZnO, Example A[1] | | 4 | |
| Nano ZnO, Example B[1] | | | 4 |
| Resin PA 565[1] | 30 | 30 | 30 |
| Ethyl acetate | 136 | 136 | 136 |
| Solvent naphtha | 136 | 136 | 136 |
| Toluene | 68 | 68 | 68 |
| Phasing (in days) | | | |
| 90 | 5 | 0 | 0 |

[1]based in all cases on solids
[2]Bayoxide Z

Determination of Thermostability (HCl Resistance)

The samples are produced as described under section 3.3 and examined according to method 4.2

| Formulation | 9 | 10* |
|---|---|---|
| Baypren ® 233[1] | 100 | 100 |
| ZnO[1] | 2[2] | |
| Nano ZnO, Example A[1] | | 2 |
| Resistance to cleavage of HCl immediately (in mins) | 600 | 750 |
| Resistance to cleavage of HCl after 14 days (in mins) | 217 | 575 |

[1]based in all cases on solids
[2]Bayoxide Z
*= example according to the invention As example 10 according to the invention shows, the resistance to the cleavage of HCl remains.

What is claimed is:

1. A composition comprising:
   a) polychloroprene
   b) one or more organic solvents and
   c) zinc oxide particles having a weight-averaged average particle size of less than 150 nm determined by ultracentrifugation.

2. The composition according to claim 1, wherein the organic solvent comprises at least one non-polar organic solvent.

3. The composition according to claim 1, further comprising:
   d) one or more conventional adhesive auxiliaries and/or additives.

4. The composition according to claim 3, wherein at least one reactive phenol resin is added as component d).

5. The composition according to claim 3, wherein component d) comprises magnesium oxide.

6. The composition according to one of claim 1, wherein the composition contains:
   4.95 to 59.95% by weight of a) polychloroprene,
   40 to 95% by weight of b) one or more organic solvents,
   0.05 to 10% by weight of c) zinc oxide particles having a weight-averaged average particle size of less than 150 nm determined by ultracentrifugation and
   0 to 55% by weight of d) one or more conventional adhesive auxiliaries and/or additives.

7. A composition containing:
   b) one or more non-polar organic solvents and
   c) zinc oxide particles having a weight-averaged average particle size of less than 150 nm determined by ultracentrifugation.

8. The composition according to claim 1, wherein the organic solvent b) is selected from aliphatic and aromatic hydrocarbons.

9. The composition according to claim 7, wherein the composition contains:
   60 to 99% by weight of b) one or more non-polar organic solvents and
   1 to 40% by weight of c) zinc oxide particles having a weight-averaged average particle size of less than 150 nm determined by ultracentrifugation, based in each case on the total quantity of b) and c).

10. The composition according to claim 1, wherein the composition contains at least one dispersant.

11. The composition according to claim 7, wherein the composition contains at least one phenol resin.

12. The composition according to claim 1, wherein more than 95% of the solvents contained therein consist of organic solvents.

13. A process for producing the composition according to claim 7, comprising the steps:
   producing zinc oxide particles having a weight-averaged average particle size of less than 150 nm determined by ultracentrifugation in the presence of at least one polar organic solvent,
   compacting the zinc oxide particle dispersion obtained in the above step to a solids content of at least 80% by weight, and
   redispersing the zinc oxide dispersion obtained in the above step with one or more non-polar organic solvents, optionally with the addition of one or more dispersants.

14. Solvent-containing adhesive compositions comprising the composition according to claim 7.

15. A method of improving the storage stability of an adhesive composition comprising adding the composition according to claim 7 to a solvent-containing adhesive composition.

16. A method of making an adhesive composition comprising adding the composition according to claim 7 to a solvent-containing adhesive compositions based on polychloroprene.

17. A process for producing the composition according to claim 1 comprising the steps:
   i) preparing a composition comprising b) one or more non-polar organic solvents, and c) zinc oxide particles having a weight-averaged average particle size of less than 150 nm determined by ultracentrifugation,
   ii) preparing a composition containing polychloroprene dissolved in one or more organic solvents,
   iii) mixing the compositions prepared in steps i) and ii),
   iv) optionally adding conventional adhesive auxiliaries and/or additives and
   v) optionally adding an additional solvent.

18. An adhesive or sealant composition comprising the composition according to claim 1 and auxiliaries and/or additives selected from the group consisting of fillers, resins, chlorinated rubber, anti-ageing agents, polyisocyanate crosslinking agents, solvents, plasticizers, pigments, catalysts, levelling agents, thickeners, stabilizers, light stabilizers, antioxidants, defoamers, UV absorbers, and combinations thereof.

19. A process for producing bonded substrates comprising applying at least one composition according to claim 1 to at least one surface of at least one substrate and subsequently bonding the coated substrate to at least one additional optionally coated substrate.

20. Bonded substrates obtained according to claim 19.

21. The composition according to claim 2, further comprising:
   d) one or more conventional adhesive auxiliaries and/or additives.

22. The composition according to claim 21, wherein component d) comprises magnesium oxide.

23. The composition according to claim 3, wherein the adhesive auxiliaries and/or additives are selected from the group consisting of fillers, resins, chlorinated rubber, anti-ageing agents, polyisocyanate crosslinking agents, solvents, plasticizers, pigments, catalysts, levelling agents, thickeners, stabilizers, light stabilizers, antioxidants, defoamers, UV absorbers, and combinations thereof.

24. The composition according to claim 7, wherein the organic solvent b) is selected from aliphatic and aromatic hydrocarbons.

25. The composition according to claim 7, wherein the composition contains at least one dispersant.

26. The composition according to claim 7, wherein more than 95% of the solvents contained therein consist of organic solvents.

* * * * *